United States Patent
Sonderegger et al.

(10) Patent No.: US 10,195,393 B2
(45) Date of Patent: Feb. 5, 2019

(54) ONE-PIECE MOLDED CATHETER AND METHOD OF MANUFACTURE

(75) Inventors: Ralph Lee Sonderegger, Farmington, UT (US); Weston Harding, Lehi, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 77 days.

(21) Appl. No.: 13/984,024

(22) PCT Filed: Feb. 8, 2012

(86) PCT No.: PCT/US2012/000077
§ 371 (c)(1),
(2), (4) Date: Nov. 22, 2013

(87) PCT Pub. No.: WO2012/141760
PCT Pub. Date: Oct. 18, 2012

(65) Prior Publication Data
US 2014/0074028 A1    Mar. 13, 2014

Related U.S. Application Data

(60) Provisional application No. 61/441,258, filed on Feb. 9, 2011.

(51) Int. Cl.
*A61M 25/06* (2006.01)
*A61M 25/00* (2006.01)
(Continued)

(52) U.S. Cl.
CPC .......... *A61M 25/001* (2013.01); *A61M 5/158* (2013.01); *A61M 25/0009* (2013.01);
(Continued)

(58) Field of Classification Search
CPC .............. A61M 5/158; A61M 25/0009; A61M 25/0606; A61M 2005/1585;
(Continued)

(56) References Cited

U.S. PATENT DOCUMENTS 5,620,639 A * 4/1997 Stevens ................ A61M 5/158
264/504
2002/0095138 A1  7/2002 Lynch et al.
(Continued)

FOREIGN PATENT DOCUMENTS

EP       1820525        8/2007
EP       1820525 A1     8/2007
(Continued)

*Primary Examiner* — Nathan R Price
*Assistant Examiner* — Anh Bui
(74) *Attorney, Agent, or Firm* — Dickinson Wright, PLLC (57) ABSTRACT

A one-piece catheter (30) and manufacturing method therefor are disclosed. The catheter (30) includes a catheter tube (33) and an adapter (31). The catheter catheter tube (33) includes a tip (331) at one end and an end portion (332) at another other end. The adapter (31) can be configured for receiving a septum (402). The adapter (31) includes a narrow opening. The end portion (332) of the catheter tube (33) is connected to the adapter (31) at the narrow opening for fluid communication between the catheter tube (33) and the adapter (31). The catheter tube (33) and adapter (31) are formed as a one-piece element that is preferably injection molded in a single-shot process. Additional elements, such as one or more retention tabs (313) for attaching to a base can be formed on the catheter (30). The one-piece catheter (30) can be made by a single-shot injection molding process. Additional structures, such as a base can be attached to the catheter (30) by a second-shot injection molding process.

8 Claims, 10 Drawing Sheets

(51) Int. Cl.
  *A61M 5/158* (2006.01)
  *B29C 45/00* (2006.01)
  *B29C 45/16* (2006.01)
  *B29L 31/00* (2006.01)

(52) U.S. Cl.
  CPC ......... *A61M 25/0606* (2013.01); *B29C 45/00* (2013.01); *A61M 25/0097* (2013.01); *A61M 2005/1581* (2013.01); *A61M 2005/1585* (2013.01); *A61M 2005/1587* (2013.01); *A61M 2207/00* (2013.01); *B29C 45/1615* (2013.01); *B29L 2031/7542* (2013.01)

(58) Field of Classification Search
  CPC .... A61M 2005/1581; B29L 2031/7542; B29C 45/1615
  See application file for complete search history.

(56) References Cited

U.S. PATENT DOCUMENTS

| | | | |
|---|---|---|---|
| 2004/0158207 A1* | 8/2004 | Hunn | A61M 5/158 604/164.01 |
| 2005/0101932 A1* | 5/2005 | Cote | A61M 5/158 604/506 |
| 2007/0049870 A1 | 3/2007 | Gray et al. | |
| 2007/0112303 A1 | 5/2007 | Liniger | |
| 2007/0135774 A1 | 6/2007 | Turner et al. | |
| 2007/0185454 A1 | 8/2007 | Fangrow, Jr. | |
| 2009/0048578 A1 | 2/2009 | Adams et al. | |
| 2009/0062767 A1 | 3/2009 | Van Antwerp et al. | |
| 2010/0022956 A1 | 1/2010 | Tipsmark et al. | |
| 2016/0303346 A1* | 10/2016 | Fentress | A61M 25/0009 |

FOREIGN PATENT DOCUMENTS

| | | |
|---|---|---|
| JP | 8-507477 | 8/1996 |
| JP | H9-109187 | 4/1997 |
| JP | 2002-095754 A | 4/2002 |
| JP | 2004-524926 A | 8/2004 |
| JP | 2004-329922 | 11/2004 |
| JP | 2005-515798 A | 6/2005 |
| JP | U3118321 | 1/2006 |
| JP | 2007-510497 A | 4/2007 |
| JP | 2010532243 | 10/2010 |
| JP | 2010533525 A | 10/2010 |
| JP | 2014-510574 A | 5/2014 |
| WO | WO-2008122983 A1 | 10/2008 |
| WO | WO-2009098291 A1 | 8/2009 |
| WO | WO-2009139857 A1 | 11/2009 |

* cited by examiner

ONE-PIECE MOLDED CATHETER AND METHOD OF MANUFACTURE

CROSS-REFERENCE TO RELATED APPLICATION

This application claims the benefit of U.S. Provisional Application No. 61/441,258, filed on Feb. 9, 2011, and International Application No. PCT/US2012/000077, filed Feb. 8, 2012 in the U.S. Patent and Trademark Office, the disclosure of said application being incorporated herein by reference in its entirety.

FIELD OF THE INVENTION

The present invention relates to medical catheters and methods of manufacture thereof that minimize the number of components without compromising the functionality of the catheters.

BACKGROUND OF THE INVENTION

Catheters are widely used in the medical applications. Peripheral or intravenous catheters and infusion set catheters are two frequently used types of catheters. Peripheral or intravenous (IV) catheters infuse medication or other fluids directly into blood vessels. Infusion set catheters are integral parts of infusion sets that deliver medication, such as insulin, into the skin for absorption by the user.

Figure 1:
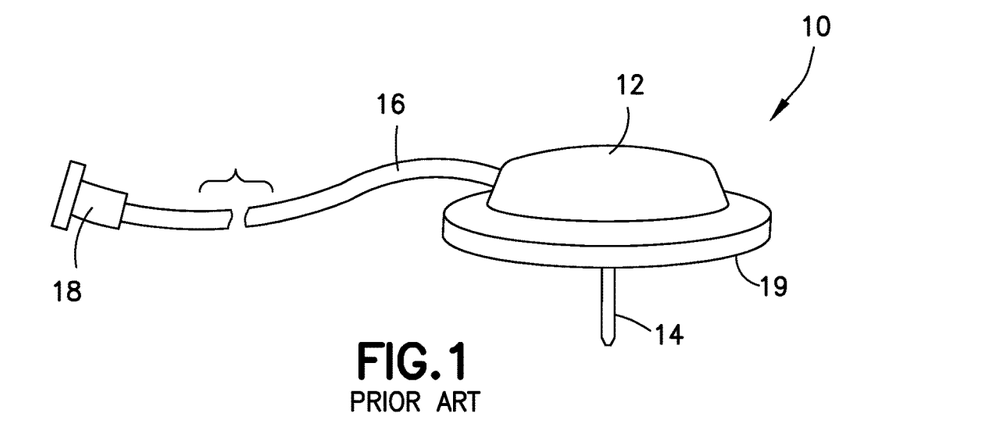
FIG. 1 is a perspective view of a conventional infusion set.

FIG. 1 illustrates a conventional infusion set 10 for use with an infusion set catheter to deliver insulin therapy. The infusion set 10 comprises an extension set, a base 19 and a catheter 14 attached to the base 19. The extension set comprises a hub 12, connector 18, fluid line tube set 16 connecting the hub 12 and the connector 18, and a pump (not shown) connected to the connector 18, such that insulin from the pump is delivered through the catheter 14. An insertion device inserts or attaches the catheter to a user. The infusion set and insertion device can also be combined into one unit.

Another type of insulin infusion device is a patch pump. Unlike a conventional infusion pump, a patch pump is an integrated device that combines most or all of the fluid components in a single housing which is adhesively attached to an infusion site, and does not require the use of a separate infusion (tubing) set. A patch pump adheres to the skin, contains insulin (or other medication), and delivers the drug over a period of time, usually via an integrated subcutaneous catheter. Patch pump and infusion sets need to be reapplied on a frequent basis, such as every three days, as complications may otherwise occur.

Catheters used in infusion sets and patch pumps are similar in construction to peripheral or IV catheters, with the infusion set catheters generally being smaller in size.

Figure 2:
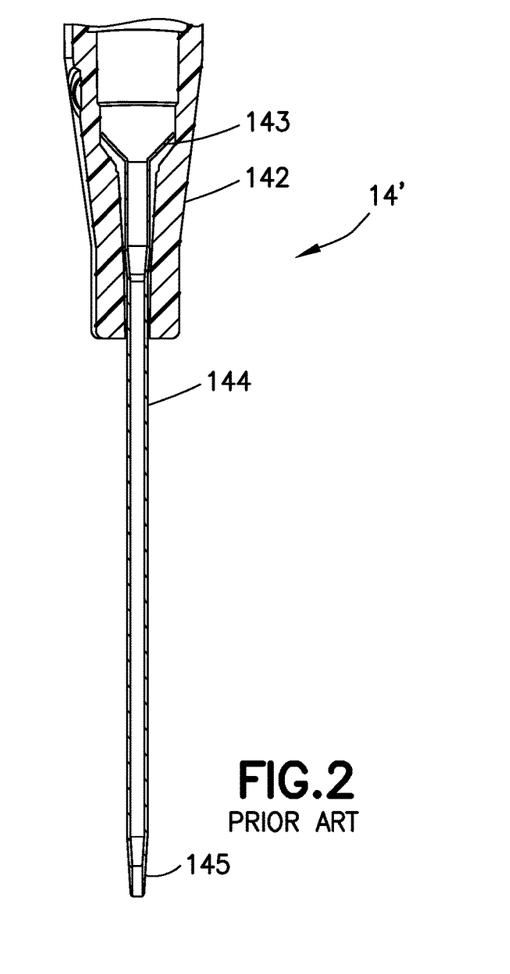
FIG. 2 is an enlarged cross-sectional view of an end portion of a conventional peripheral or intravenous catheter.

A conventional peripheral or IV catheter is illustrated in FIG. 2. The peripheral catheter 14' is generally made of a polymer, such as Teflon®. The catheter tube 144 is conventionally connected to a rigid metal or plastic wedge 143 which is a funnel-shaped device that attaches the catheter to an adapter or hub 142 of the catheter. A neck portion of the wedge 143 is inserted into an end portion of the catheter tube 144 and the catheter is deformed to frictionally wedge itself into the catheter adapter 142. The catheter 14' includes an open distal tip 145.

In such construction, transmission of impact or vibration forces can damage the catheter at the point of impact as well as at its connection to the wedge, resulting in a weakened connection and/or leaks at the connection. The weakened connection between the catheter and the wedge may also cause the catheter to break off from the wedge during use.

Figure 3:
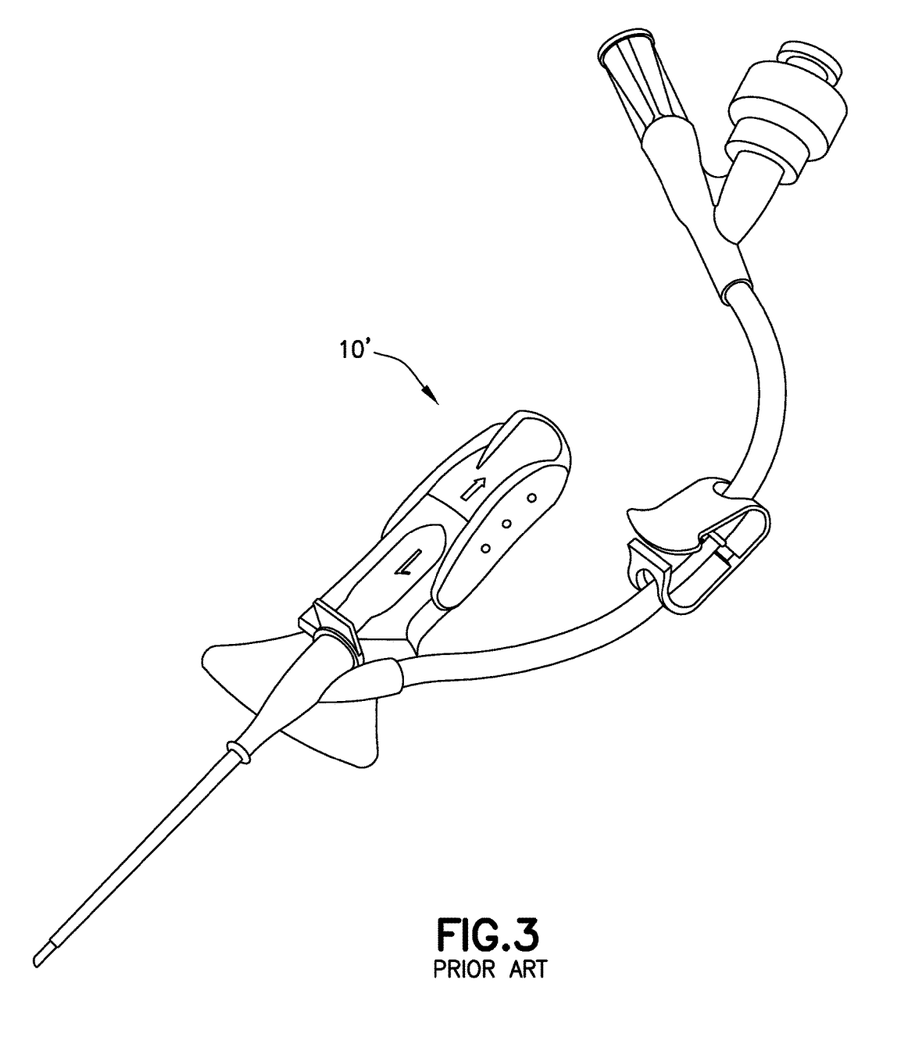
FIG. 3 is a perspective view of a complete peripheral or intravenous catheter assembly.

A complete IV catheter assembly 10' is illustrated in FIG. 3. This device is available as the BD Nexiva™ Closed IV Catheter System from Becton, Dickinson and Company (BD). The indwelling catheter portion is made of BD's ViaIon™ biomaterial that reduces mechanical phlebitis (caused by irritation of the venous endothelium by the catheter) and infiltration (which occurs when an IV fluid or medication accidentally enters the surrounding tissue rather than the blood vessel), maximizes dwell time, provides kink resistance (resistance of the catheter to be subject to becoming snagged, knotted or sharply bent to form a kink which impedes or blocks fluid flow) and recovery from kinks, and softens in the vessel.

Conventional infusion set and/or patch pump catheters, as well as peripheral or intravenous catheters, are susceptible to damage with normal wear, such as kinking. Conventional infusion set catheters are also sometimes fragile due to their construction and material, and are susceptible to damage due to excessive bounce or vibration in the insertion mechanization of the catheter, via an introducer needle, which may result in excessive force being transmitted to the catheters.

SUMMARY OF THE INVENTION

An object of the present invention is to provide a catheter configured and arranged to optimize column strength for catheter insertion, flexibility for user comfort, and tensile strength for durability, insertion and removal, while minimizing the number of components.

These and other objects are substantially achieved by providing a catheter whose construction is simplified by combining conventional components into a molded, one-piece unit that combines the functions of the adapter, wedge and catheter tubing, and that can increase overall strength of the structure at key points to prevent leakage of medication through the catheter.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF THE EXEMPLARY EMBODIMENTS

Figure 4:
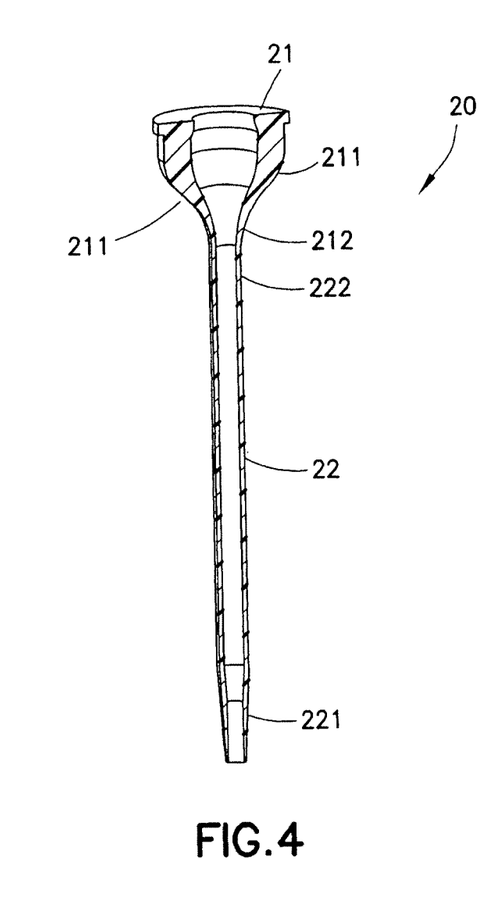
FIG. 4 is an enlarged cross-sectional view of an exemplary one-piece catheter that includes a base structure in accordance with an embodiment of the present invention.
Figure 5:
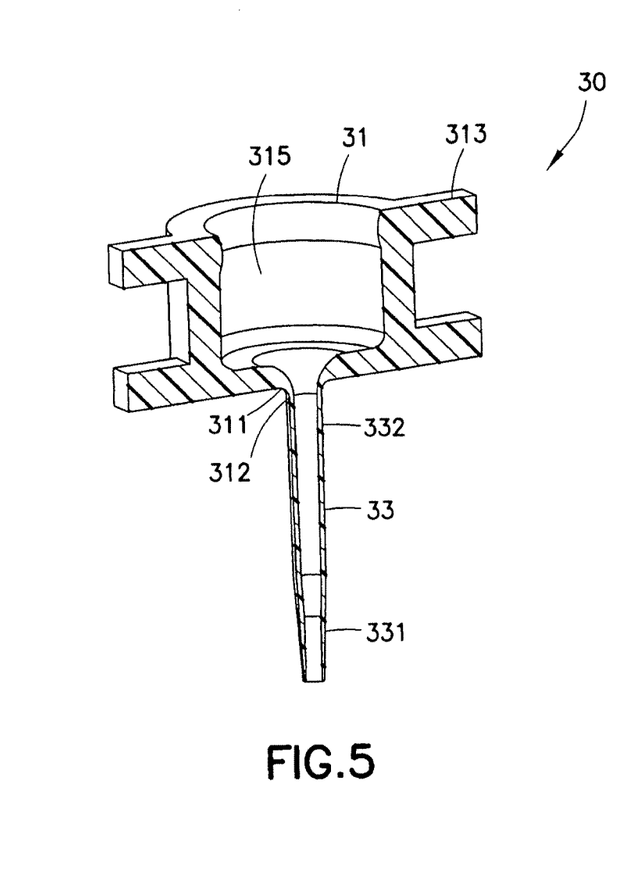
FIG. 5 is an enlarged cross-sectional view of an exemplary one-piece catheter that includes a base structure in accordance with an embodiment of the present invention.
Figure 6:
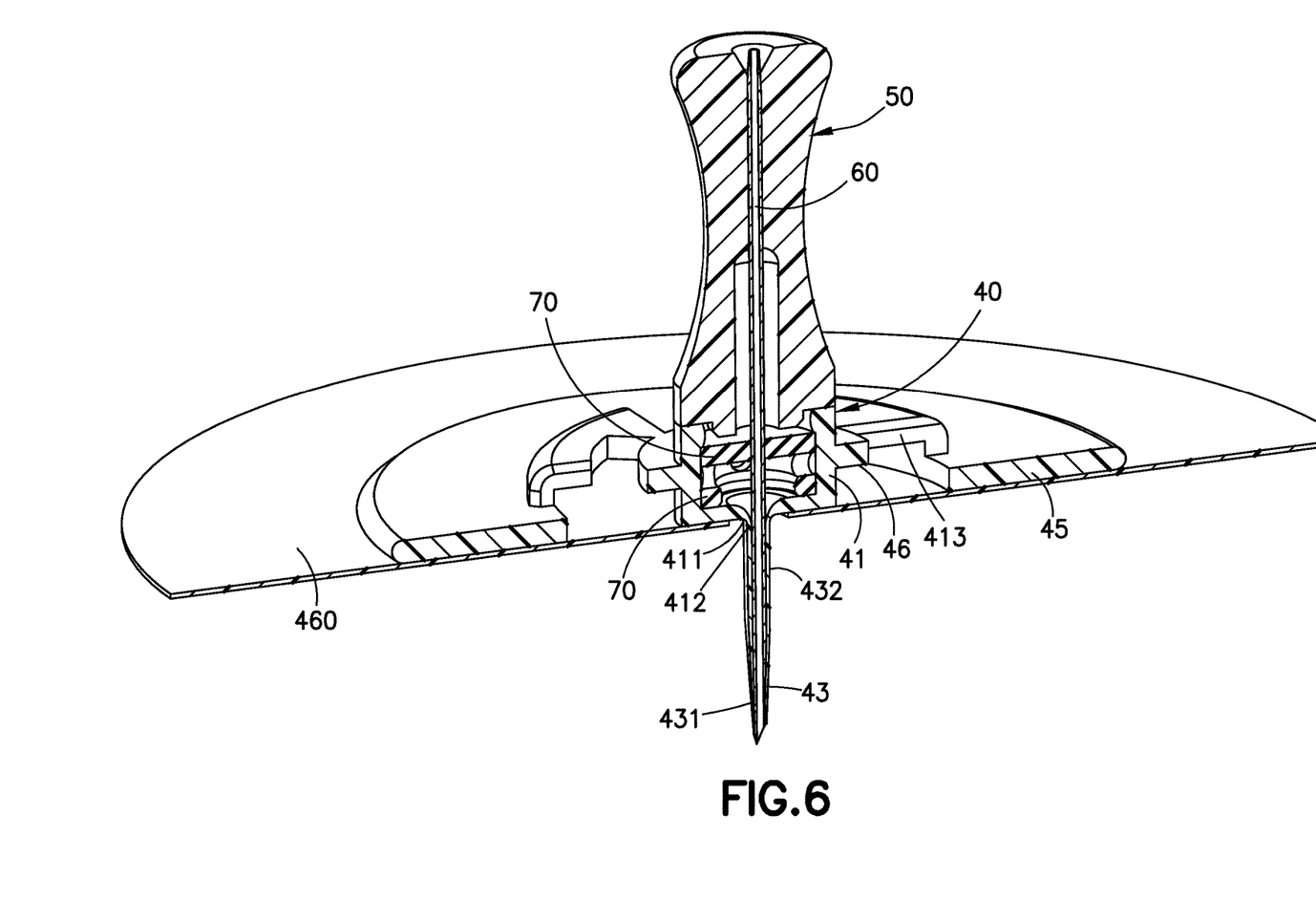
FIG. 6 is an enlarged cross-sectional view of an infusion set which includes an exemplary one-piece catheter in accordance with an embodiment of the present invention.

In exemplary embodiments of the present invention, as illustrated in FIGS. 4-6, the adapter and catheter are molded in a single unit, eliminating the need for the manufacture and assembly of separate components that include the adapter, catheter tubing, wedge, as well as various tipping operations such as flaring, swaging, cutting and RF tipping operations. In addition, more complex geometries may be molded into the catheter adapter, such as retention tabs for locking the catheter to a base, as illustrated in FIGS. 5 and 6, as well as one or more side ports for communicating with the fluid connector of an infusion set.

FIG. 4 illustrates one embodiment of the present invention that improves the manufacturing process for a catheter. In the exemplary catheter 20 illustrated in FIG. 4, the catheter tube 22 is molded together with the adapter 21, preferably in a single-shot injection molding process, in which a polymer material is heated to a desired temperature before being injection molded. Such single-shot injection molding process can also be used to make an IV catheter, similar to that which is illustrated in FIG. 2. As illustrated in FIG. 4, the adapter 21 includes a lead-in portion 211 that is illustrated as having a funnel shape. The cross-sectional view illustrated in FIG. 4 further illustrates that at the apex 212 of the adapter 21, the end portion 222 of the catheter tube 22 is connected (fused together) to the adapter 21, such that the catheter 20 is a single piece. At the opposite end of the catheter tube 22, away from the end portion 222, is the open distal tip 221 of the catheter 20, through which liquid medication is administered to the patient.

With reference to FIG. 4, the embodiment illustrated in the drawing can be molded with a single-shot injection process, by using a molding process wherein pressure is built up and then released quickly. For the embodiment illustrated in FIG. 4, it is preferable to gate in two locations, symmetrically positioned in the adapter area, in order to equalize the pressure on both sides of the core pin, and thus reducing bending of the core pin.

The cross-sectional view in FIG. 5 illustrates another exemplary embodiment of the present invention, adapted for use in an infusion set. The catheter 30 illustrated in FIG. 5 includes an adapter 31 sized and configured for receiving a septum (not shown) in the cylindrical main cavity 315 thereof. In addition, the adapter 31 includes radially extending retention tabs 313 that are configured for attaching to and or being guided to a base (see FIGS. 9A and 10). At the lower portion of the adapter 31, a funnel-shaped lead-in portion 311 is formed that connects to the end portion 332 of the catheter tubing 33. The catheter tube 33 is shortened in length, as compared with that of the embodiment illustrated in FIG. 4. A fluid pathway extends from the open distal tip 331 of the catheter tube 33 through the lead-in portion 311. The apex 312 of the lead-in portion 311 is the site of connection to the end portion 332 of the catheter tube 33. As in the embodiment of FIG. 4, the exemplary catheter 30 illustrated in FIG. 5 is a one-piece design that is preferably molded in a single shot.

Figure 9A:
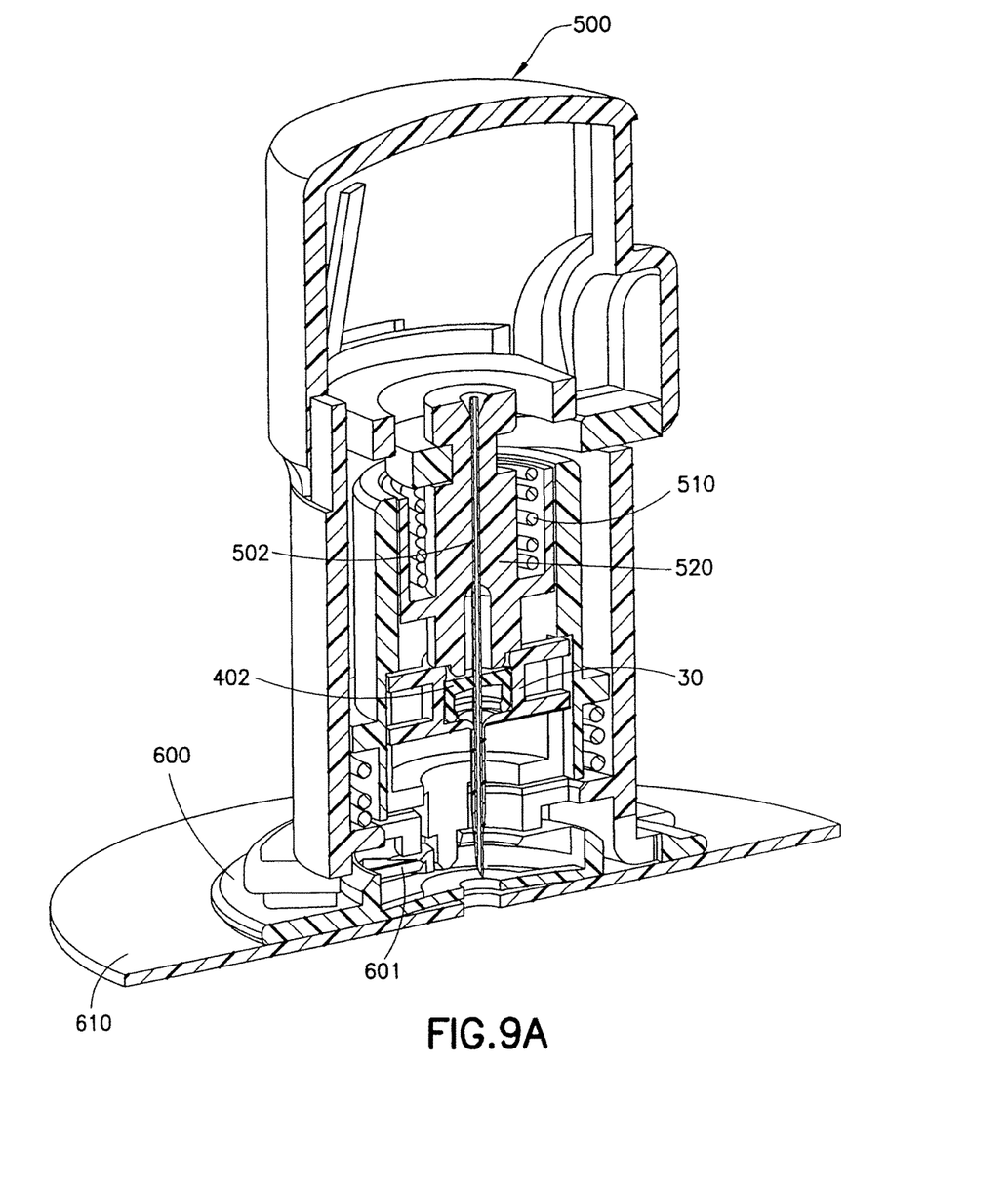
FIG. 9A is an enlarged cross-sectional view of an introducer device primed to insert an exemplary one-piece catheter in accordance with an embodiment of the present invention.
Figure 10:
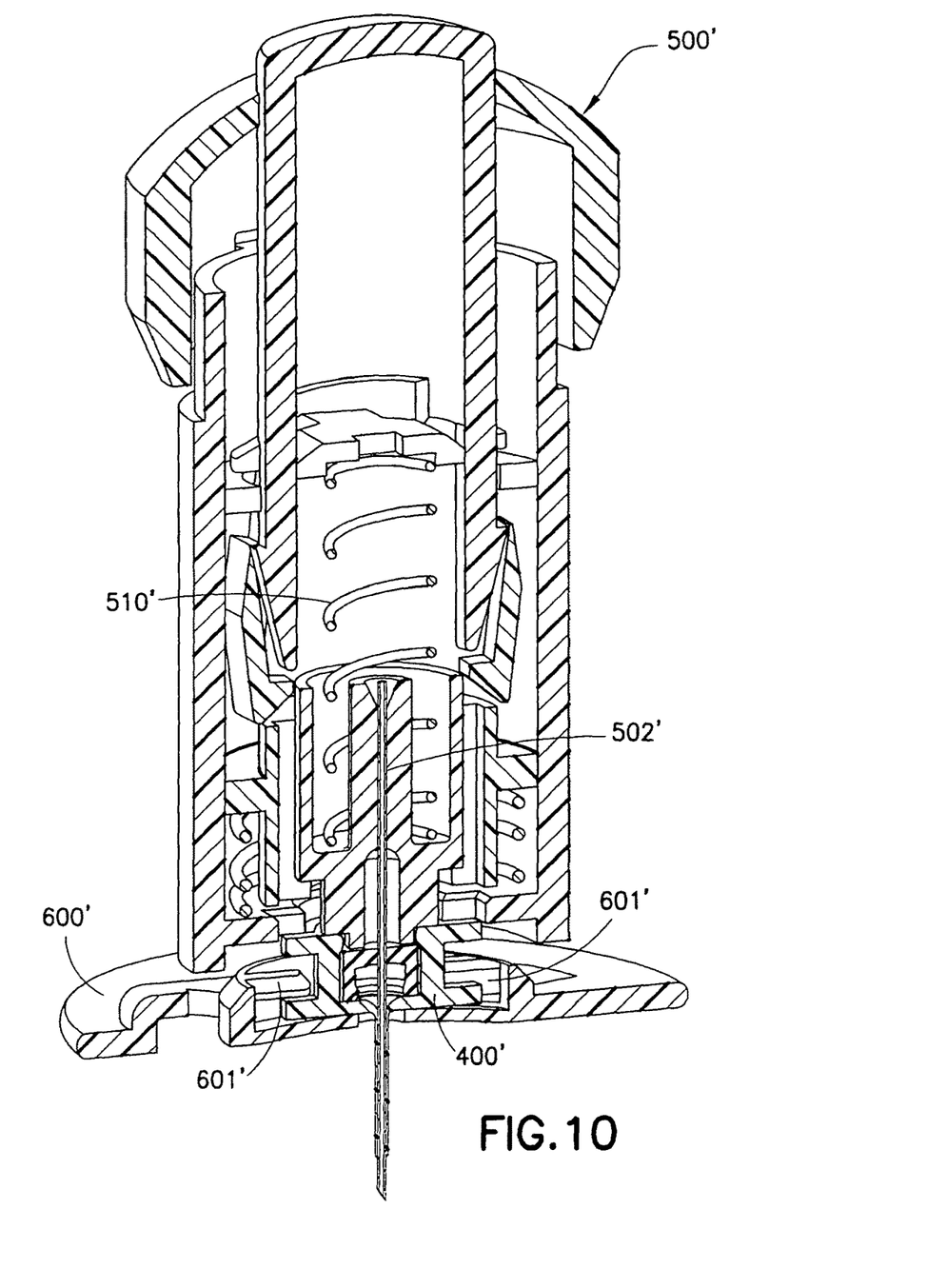
FIG. 10 is a cross-sectional view of the introducer device of FIGS. 9A and 9B after the needle base has fired.

As illustrated in FIGS. 9A and 10, a septum 402 is received in the adapter 31 of the catheter 30. The retention tabs 313 are slotted between the guides 601, 601' of the base 600, 600', such that after the introducer 500, 500' has fired to insert the introducer needle 502, 502' with the catheter 30 into a user, the retention tabs 313 are secured to the base 600, 600' by the guides 601, 601'.

There are several advantages to the one-piece catheter design of the present invention. The one-piece catheter design does away with the need for a wedge that is required in a conventional catheter (as illustrated in FIG. 1) for attachment to a catheter base. Such wedge is usually made of a metal or other hardened material, requiring the use of additional materials and processes for the construction of a conventional catheter.

In contrast, in an exemplary embodiment of the present invention, the one-piece catheter 20, 30 can use only one material, such as a polymer, reducing the cost of production. In addition, since the exemplary embodiment of the present invention is a one-piece design, it does away with the multiple components of a conventional catheter design.

FIG. 6 illustrates an enlarged cross-sectional view of an infusion set with an exemplary one-piece catheter similar to that of FIG. 5. In the embodiment illustrated in FIG. 6, the catheter 40 includes a catheter tube 43 and an adapter 41. The catheter 40 is attached to a base 45. The catheter 40 and base 45 can, if desired, be molded together to form a single unit catheter-base assembly via a single-shot molding process. The catheter-base assembly can also be formed by a two-shot molding process in which the first-shot molding process, using a heated polymer made of a material appropriate for extended indwelling in a user, forms the catheter 40. Thereafter, a second molding process, using a heated polymer that may be the same or different from that used in the first-shot, forms and attaches the base 45 to the catheter 40. Alternatively, the base 45 can be formed in the first molding process and the catheter can be formed and attached to the base 45 in the second-shot molding process. The injection molding of components may reduce costs by simplifying the manufacturing process.

In a single-shot molding process, a polymer is heated to a temperature suitable for the process and injection molded to form a first element (e.g., a catheter). If an additional molding process is required in order to add a second element (e.g., a base) to the first element, the same or a different polymer can be heated to a temperature suitable for a second-shot molding process and injection molded to form the second element. The second-shot molding process also fuses the first element to the second element. The polymers used in the molding processes can utilize same or different materials and they can have the same color or different colors if desired to clearer visual identification. A preferred polymer for injection molding the catheter is Teflon®. If Teflon® is used to injection mold the catheter, the base can also be made of Teflon ® or another polymer, e.g., a polyurethane product such as Vialon™ biomaterial by Becton, Dickinson and Company (BD).

The catheter can also be formed using a multiple-shot molding process, in which various components can be molded in sequence. For instance, the catheter tube and adapter could be made from different materials using a two-shot molding process.

The embodiment of FIG. 6 illustrates a catheter infusion set that features manual insertion and needle removal via the catheter tube 43, followed by attachment of a removable infusion fluid connector and tube set (not shown).

In FIG. 6, the one-piece catheter 40, preferably molded using a polymer such as Teflon®, includes a base 45 made of the same polymer or a different polymer if a two-shot molding process is used. A septum 70 is placed in the main cavity of the adapter 41, through which an introducer needle 60 is shown penetrating. The introducer needle 60 is shown in its housing, the needle handle or base 50. The introducer needle 60 attached to the needle handle 50 is detachable from the catheter 40. The catheter 40 includes a retention ring 46 that connects the adapter 41 to the base 45. The adapter 41 may include a slotted ring-like structure or flange 413 that can attach to or connect to a tube set connector (not shown) to receive fluid into the adapter such that the fluid can flow through the catheter tube 43.

The connection between the adapter 41 to the catheter tube 43 in the embodiment illustrated in FIG. 6 is similar to that of FIG. 5. At a lower portion of the adapter 41, there is a funnel-shaped lead-in portion 411 having an apex 412. At the apex 412, and end portion 432 of the catheter tub 43 is connected to the adapter 41. The open distal tip 431 of the catheter tube 43 is also illustrated in FIG. 6, through which fluid flows outward from the inner walls of the adapter 41 through the lead-in portion 411 and the catheter tube 43. A skin adhesive 460 detachably attaches the base 45 to a user. The catheter 40 can be formed in a single-shot molding process and the base 45 can be formed by a second-shot molding process, to form the catheter-base structure.

Figure 7:
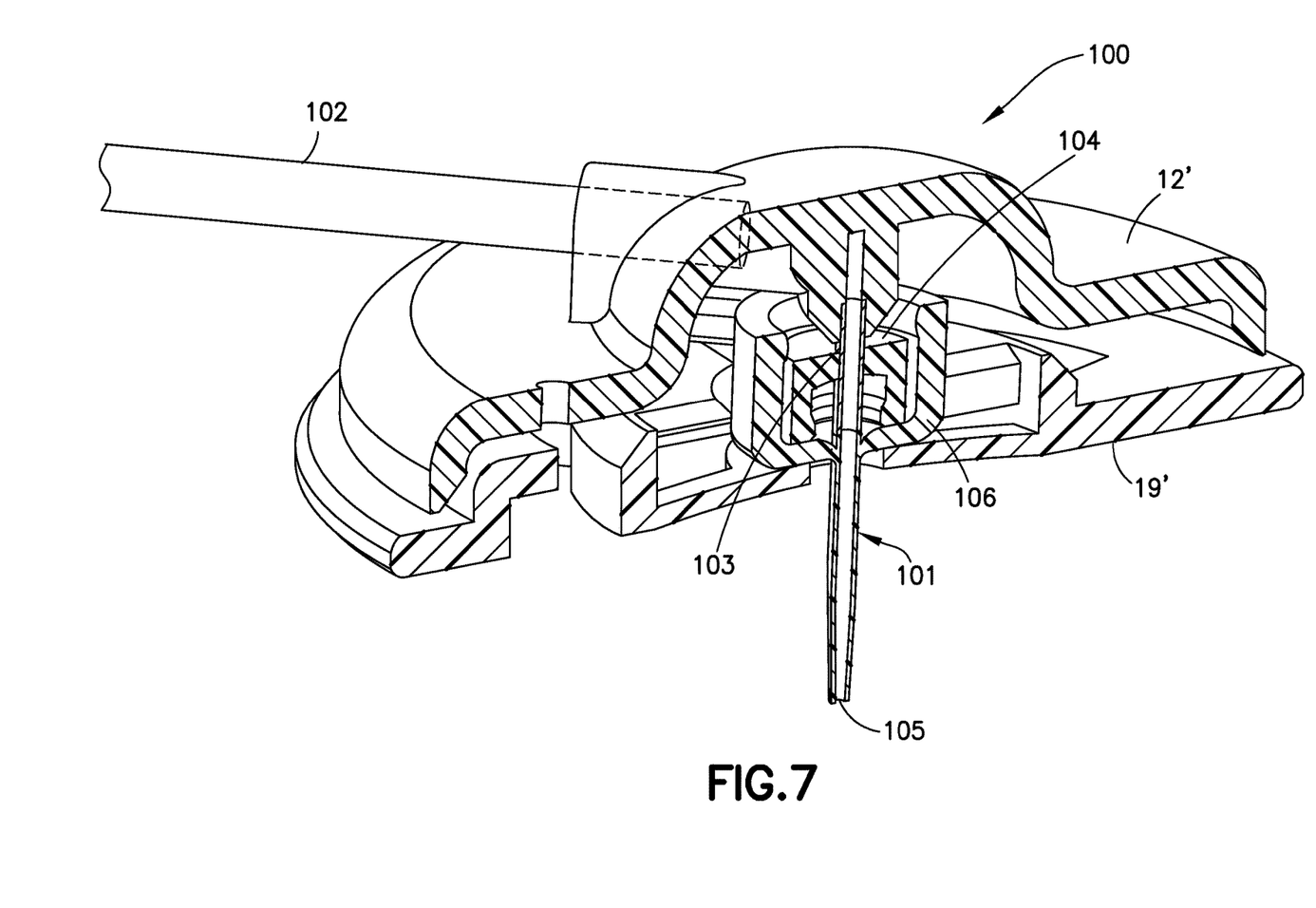
FIG. 7 is an enlarged cross-sectional view of an infusion set with an exemplary one-piece catheter in accordance with an embodiment of the present invention.

FIG. 7 is a cross-sectional view of an exemplary infusion set, wherein the infusion set 100 utilizes another one-piece catheter 101 in accordance with an exemplary embodiment of the present invention. The catheter 101 can be used as replacement for a conventional catheter having multiple components, as described above. FIG. 7 further illustrates a fluid connector or tube set 102 with a blunt cannula 103 of the hub 12' piercing a septum 104 housed in the adapter/base 106 of the catheter 101, such that when the hub 12' is removed from the base 19', the septum 104 self-closes to prevent entry of foreign particles into the catheter 101. When the hub 12' is attached to the base 19', a fluid path is formed from the tube set 102 to the external tip 105 of the catheter 101.

Figure 8A:
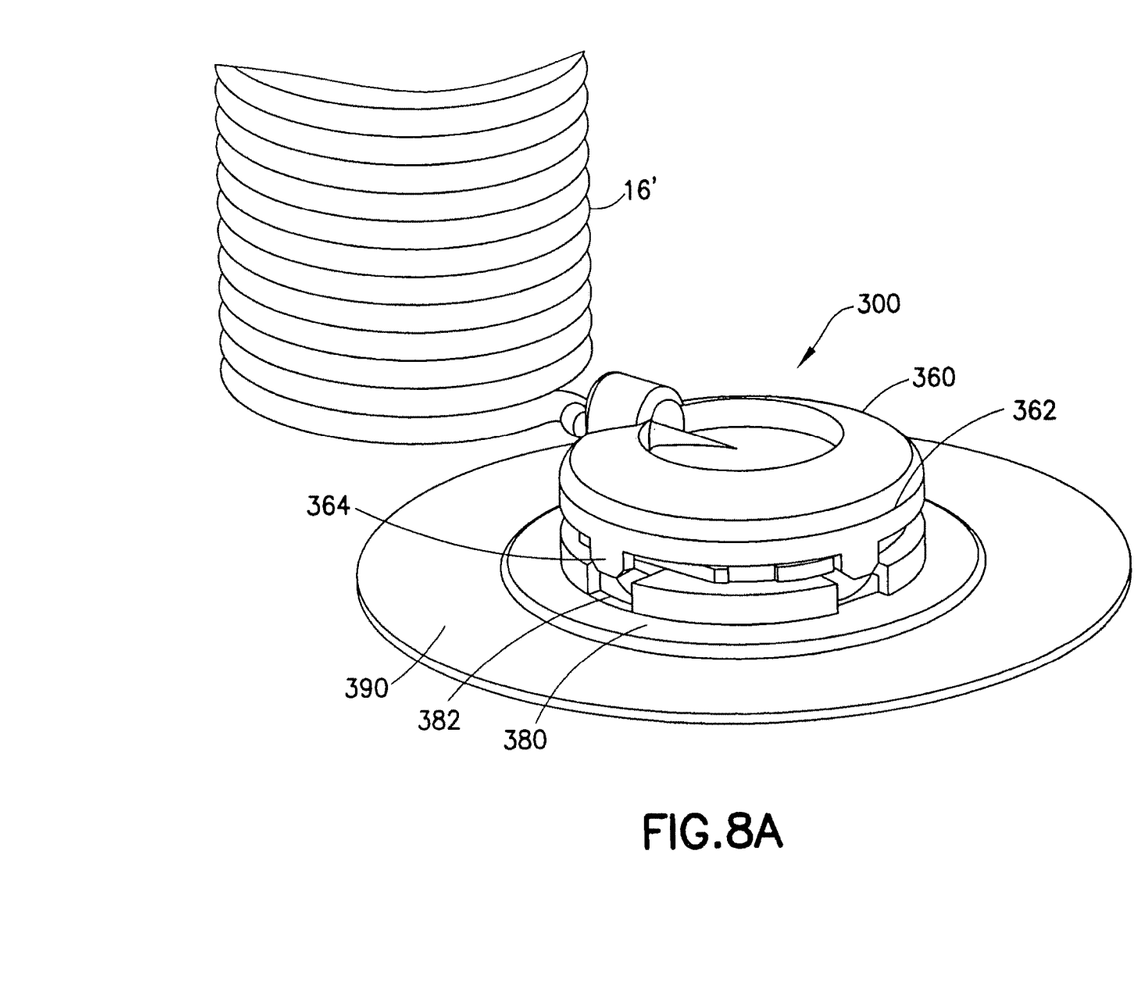
FIG. 8A is a perspective view of an infusion set.
Figure 8B:
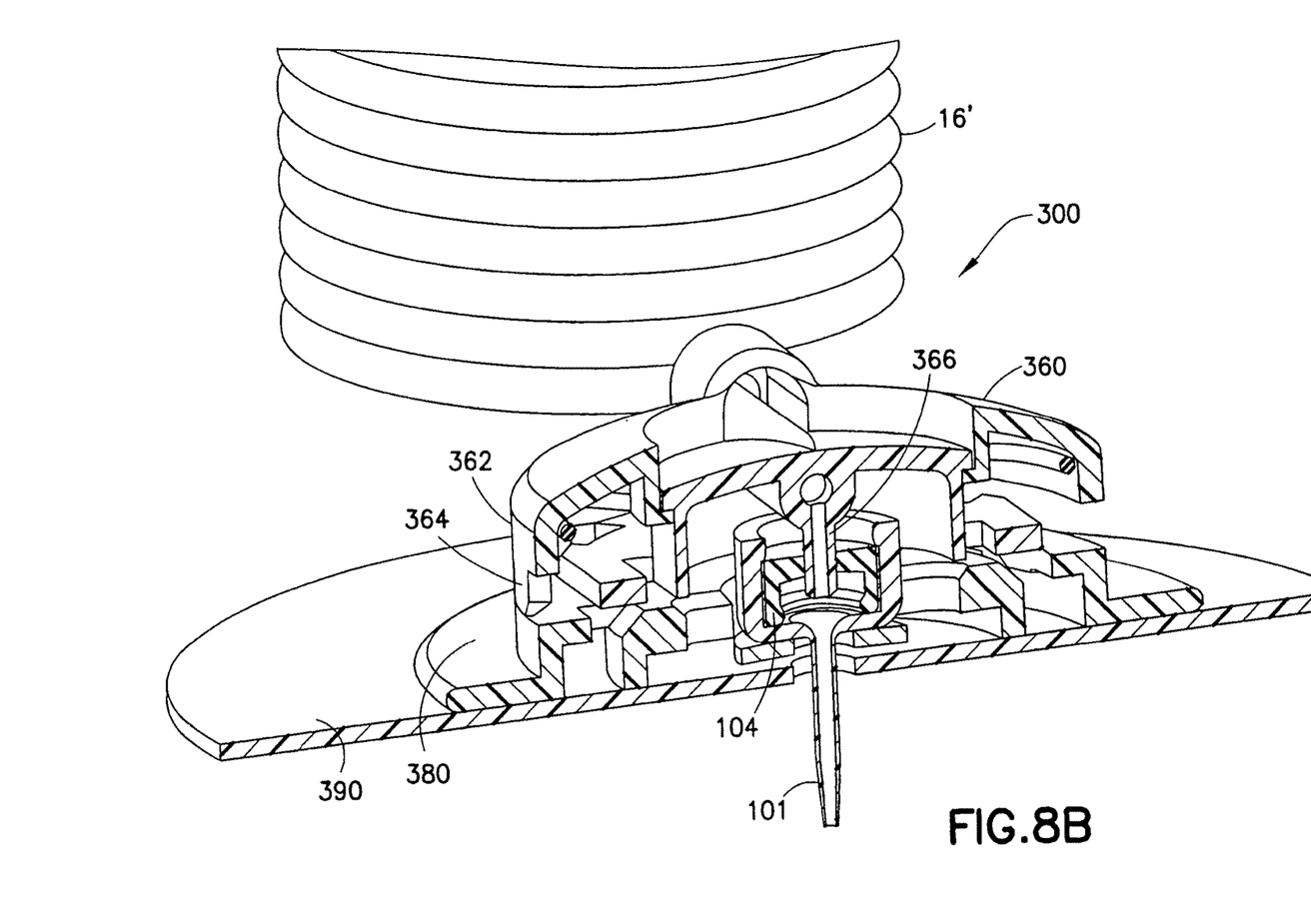
FIG. 8B is a cross-sectional view of the infusion set of FIG. 8A.

FIGS. 8A and 8B further illustrate another exemplary infusion set 300, in which a one-piece catheter 101 similar to that of FIG. 7 is utilized. In FIG. 8A, the user can attach or detach the hub 360 to or from the base 380. The hub 360 includes a locking ring 362 with tabs 364 that secure to corresponding slots 382 of the base 330. After the tabs 364 are inserted into the slots 382, the user can rotate the hub 360 to interlock tabs 364 to the base 380. A catheter 101 is secured to the base 380. FIG. 8B is a cross-sectional view of the infusion set of FIG. 8A. A skin adhesive 390 detachable attaches the base 380 to a user. As illustrated in FIG. 8B, the catheter 101 includes a cylindrical main cavity in which the septum 104 is received. When the hub 360 is attached to the base 380, the blunt cannula 366 of the hub 360 penetrates the septum 104, to permit liquid medication to be pumped into the catheter 104. Liquid medication is pumped from the pump (not shown) through the tube set 16' and into the blunt cannula 366, and exits the catheter 101.

Figure 9B:
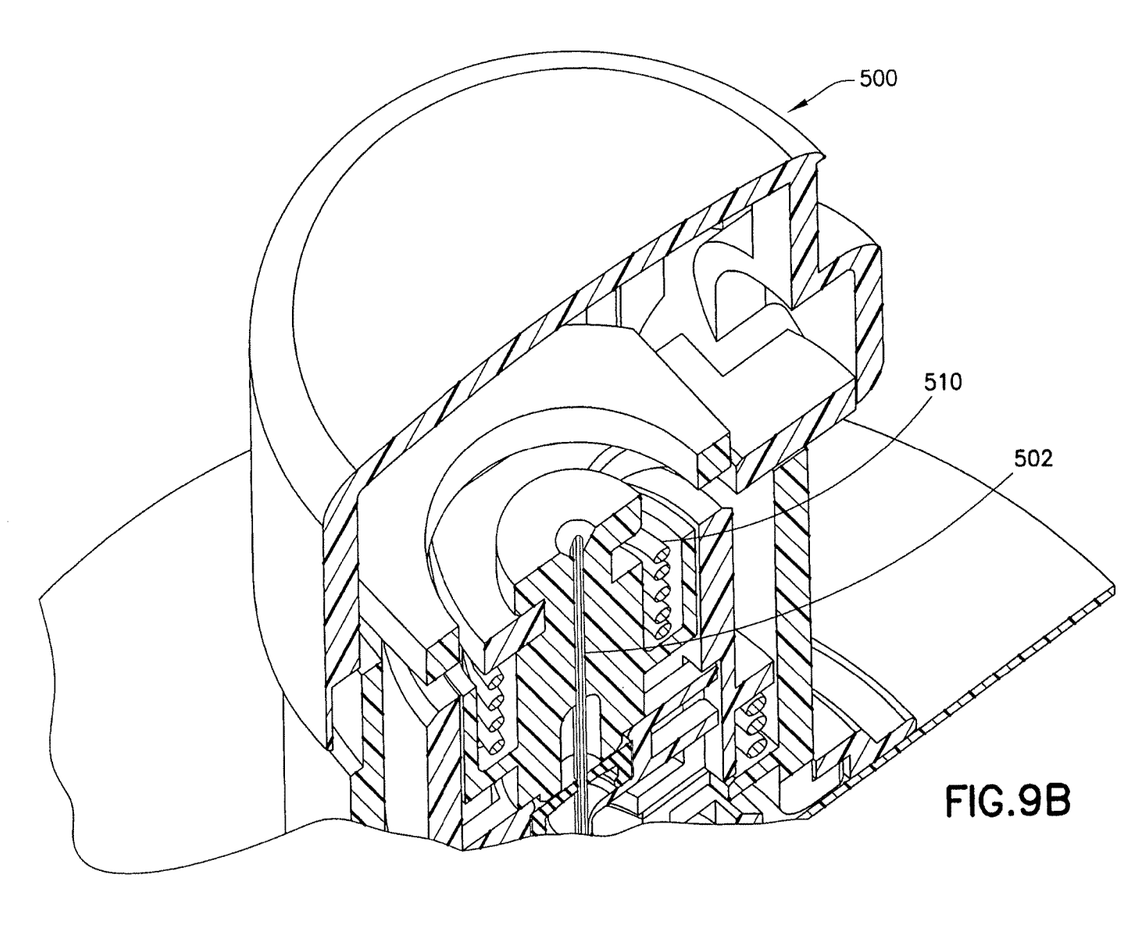
FIG. 9B is an enlarged cross-sectional view of the insulin device of FIG. 9A.

FIGS. 9A and 9B illustrate how an exemplary one-piece catheter 101 in accordance with an embodiment of the present invention, housing a septum 402 in the adapter portion thereof, can be used with an introducer 500 having a needle handle 520 with an introducer needle 502, above a base 600 to which a skin adhesive 610 is attached. The introducer 500 is spring-loaded and ready to be released to insert the catheter 400 and the introducer needle 502 into a user. FIG. 9B shows greater detail of the spring-loaded mechanism 510 that when actuated, inserts the catheter 400 and the introducer needle 502 in to a user.

FIG. 10 illustrates the insertion of a one-piece catheter 101, one that is similar to the embodiment of FIGS. 9A and 9B, in which the one-piece catheter 400', as well as an introducer needle 502', is inserted into a user by releasing a spring-loaded mechanism 510' of the introducer 500'. Upon insertion of the introducer needle 502' and the catheter 400' to a user, the introducer 500' and the introducer needle 502' are then removed from the catheter 400' which is locked or lockable to a base 600', as illustrated.

There are many advantages of a one-piece catheter. For instance, the overall strength of the one-piece catheter can generally be stronger than a conventional multi-piece assembly that utilizes polymeric and metal components. In addition, by eliminating numerous components of different materials, sizes and shapes, there is a reduction in manufacturing cost. Additionally, in exemplary embodiments of the one-piece catheter of the present invention, since there are no connection junctions, as in the frictional engagement of the conventional catheter to the conventional wedge, which minimizes the likelihood of leaks that may otherwise occur at such junctions. Further, the exemplary one-piece catheter can more evenly transmit impact forces onto the overall catheter as the catheter is inserted into a user, as compared with a conventional multi-component catheter, such that the one-piece catheter can be inserted without being weakened at any particular location, as would be the case in a conventional, multi-component catheter.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

The invention claimed is:

1. A one-piece catheter, comprising:
a single molded element comprising both a catheter tube portion and
an adapter portion;
the single molded element being a unitary structure;
the adapter portion comprising a retention tab configured to lock with a base of an infusion set, the retention tab extending radially outwardly from an outer wall of the adapter to engage a guide of the base, the guide securing the adapter to the base by preventing proximal movement of the adapter portion after the adapter portion is secured to the base, the adapter portion further comprising a cylindrical main cavity for receiving a septum;
wherein an end portion of the catheter tube portion is connected to the adapter portion for fluid communication between the catheter tube portion and the adapter portion; and
wherein the adapter portion comprises a lead-in portion that smoothly transitions from the cylindrical main cavity to a narrow opening at a proximal end of the catheter tube portion.

2. The one-piece catheter as claimed in claim 1, wherein the lead-in portion comprises a wide mouth and a narrow stem.

3. The one-piece catheter as claimed in claim 2, wherein the end portion of the catheter tube portion is connected to the adapter portion at the narrow stem of the lead-in portion.

4. The one-piece catheter as claimed in claim 1, wherein the adapter portion comprises an opening configured to be in fluid communication with a tube set that is connected to the adapter portion.

5. The one-piece catheter as claimed in claim 1, wherein the adapter portion comprises a side port in communication with a tube set.

6. The one-piece catheter as claimed in claim 1, wherein the catheter tube portion and adapter portion are formed as the single molded element by a single-shot injection molding process.

7. The one-piece catheter as claimed in claim 1, wherein the catheter tube portion, adapter portion, and base are formed as the single molded element by a two-shot injection molding process.

8. The one-piece catheter as claimed in claim 1, further comprising a septum at least partially received in the adapter portion of the catheter.

* * * * *